US00PP17636P3

(12) United States Plant Patent
Gravois et al.

(10) Patent No.: US PP17,636 P3
(45) Date of Patent: Apr. 24, 2007

(54) SUGAR CANE PLANT NAMED 'L97-128'

(50) Latin Name: ***Saccharum* sp.**
Varietal Denomination: L97-128

(75) Inventors: Kenneth A. Gravois, Baton Rouge, LA (US); Keith P. Bischoff, Baton Rouge, LA (US)

(73) Assignee: Board of Supervisors of Louisiana State University and Agriculture and Mechanical College, Baton Rouge, LA (US)

( * ) Notice: Subject to any disclaimer, the term of this patent is extended or adjusted under 35 U.S.C. 154(b) by 0 days.

(21) Appl. No.: 11/015,143

(22) Filed: Dec. 17, 2004

(65) Prior Publication Data

US 2006/0150291 P1 Jul. 6, 2006

(51) Int. Cl.
*A01H 5/00* (2006.01)

(52) U.S. Cl. ..... Plt./385
(58) Field of Classification Search ..... Plt./385
See application file for complete search history.

(56) References Cited

PUBLICATIONS

Bischoff, K.P. et al., "The Development of New Sugarcane Varieties at the LSU AgCenter," J. Amer. Soc. Sugar Technol., vol. 24, pp. 142–164 (2004).

Legendre, B.L. et al., "Registration of 'HoCP85–845' Sugarcane," Crop Sci., vol. 34, p. 820 (1994).

Legendre, B.L. et al., "Registration of 'HoCP91–555' Sugarcane," Crop Sci., vol. 40, p. 1506 (2000).

Legendre, B.L. et al., "The 2003 Louisiana Sugarcane Variety Survey," Sugar Bulletin, vol. 82(9), pp. 22–28 (2004).

Milligan, S.B. et al., "Registration of 'LCP 85–384' Sugarcane," Crop Sci., vol. 34, pp. 819–820 (1994).

*Primary Examiner*—Kent Bell
*Assistant Examiner*—June Hwu
(74) *Attorney, Agent, or Firm*—John H. Runnels; Bonnie J. Davis

(57) ABSTRACT

A new variety of sugarcane, identified as 'L97-128', is disclosed having superior sugarcane rust disease resistance, and high sugar/sucrose content and cane yield characteristics.

4 Drawing Sheets

This invention pertains to a new and distinct variety of sugarcane.

BACKGROUND OF THE INVENTION

Sugarcane variety, *Saccharum* sp., is a giant, thick, perennial grass of the Gramineae family cultivated in tropical, subtropical, and some temperate regions worldwide for its sweet sap, which is a major source of sugar and molasses. Sugarcane is believed to have originated in what is now known as New Guinea.

SUMMARY OF THE INVENTION

Genus and Species Name

This new and distinct sugarcane variety, *Saccharum* sp., demonstrates superior sugarcane rust disease resistance, and early and high sugar/sucrose content and cane yield characteristics as compared to other available sugarcane varieties known to the inventors. A new variety of sugarcane identified as 'L97-128' is disclosed having high cane yield, early maturity, high sucrose content, resistance to sugarcane rust disease, and good ratooning ability.

Variety Denomination

This new and distinct sugarcane variety is identified as 'L97-128', and is characterized by its darker greenish-brown stalk.

BRIEF DESCRIPTION OF THE DRAWINGS

The file of this patent contains at least one photograph executed in color. Copies of this patent or patent application publication with color drawing(s) will be provided by the Office upon request and payment of the necessary fee.

DETAILED BOTANICAL DESCRIPTION

Figure 1:
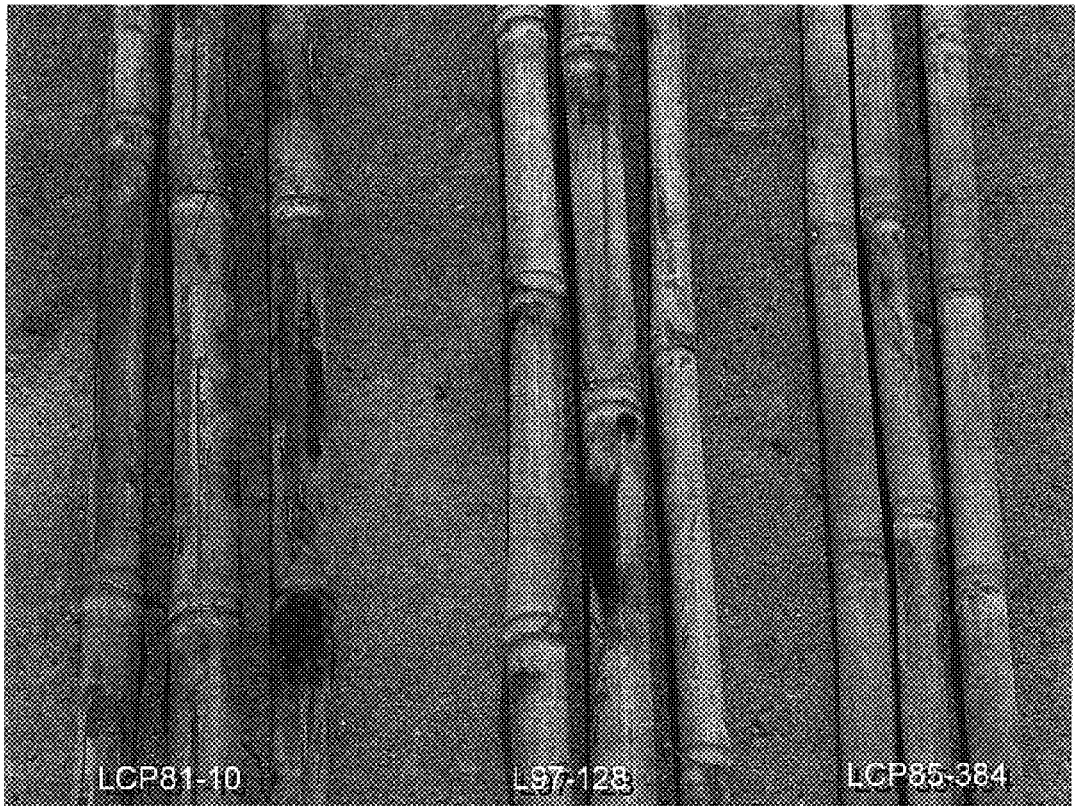
FIG. 1 is a color photograph of the stalk of the novel variety of sugarcane identified as 'L97-128' and other sugarcane varieties identified as 'LCP85-384' and 'LCP81-10', which were used for comparison tests.

This new variety of sugarcane, identified as 'L97-128', originated as a true seedling, produced by a biparental cross (identified by the inventors as 'XL92-42' (unpatented))

between the female parent 'LCP81-10' (unpatented) and the male parent 'LCP85-384' (unpatented). In this form of variety designation, which is well known among sugarcane breeders, the "L" indicates the cross and selection occurred in the sugarcane breeding program in St. Gabriel, La. The "97" indicates the year of assignment of a permanent variety identification, and "128" is a unique number assigned to varieties that year. The cross was made in 1992, in St. Gabriel, La., and this new variety was selected from among the progeny of the cross. Early stage selection among the progeny was done between the years 1992 and 1996. The seedling of 'L97-128' was germinated from a "true seed" in January 1993 and transplanted to the field in April 1993. Selection occurred in the first ratoon crop in 1994 from a single stool of sugarcane. Two stalks were cut and transplanted successfully for asexual reproduction. Asexual propagation of the new cultivar by cuttings has shown that the unique features of this new sugarcane are stable and the plant reproduces true to type in successive generations of asexual propagation. Plants described herein were characterized on Aug. 23–24, 2004 at approximately 150–165 days in age from spring emergence. The stalks characterized were from inner rows unexposed to direct sunlight. See S. B. Milligan, et al., "Registration of 'LCP 85-384' Sugarcane," *Crop Sci.,* vol. 34, pp. 819–820 (1994); and K. P. Bischoff, et al., "The Development of New Sugarcane Varieties at the LSU AgCenter," *J. Amer. Soc. Sugar Technol.,* vol 24, pp. 142–164 (2004).

'LCP81-10' never attained commercial status, but has been used as a parent in the sugarcane breeding program in St. Gabriel, La. 'LCP85-384' is one of the most widely grown commercial sugarcane varieties in Louisiana, occupying approximately 88% of the acreage devoted to sugarcane in Louisiana in 2003. The male parent exhibits high cane yield, moderately early maturity, and good ratooning ability. 'L97-128' was developed to provide a new variety with characteristics similar to 'LCP85-384', but with earlier maturity and improved sugarcane rust resistance. 'L97-128' is characterized by a darker greenish-brown stalk. The female parent (LCP81-10) exhibits similar high cane yield characteristics to that of 'L97-128', but does not possess the early and high sucrose content of its new progeny. See B. L. Legendre, et al., "The 2003 Louisiana Sugarcane Variety Survey," *Sugar Bulletin,* vol. 82(9), pp. 22–28 (2004).

Color terminology used herein is in accordance with the MUNSELL® color charts for plant tissue and the MUNSELL® Book of Color for stalk and leaf determination (Munsell Color, Gretag Macbeth LLC, New Windsor, N.Y.). The color descriptions and color illustrations are as nearly true as is reasonably possible. However, it is understood that both color and other phenotypic expressions described herein may vary from plant to plant with differences in growth, environment and cultural conditions, without any change in the genotype of the variety 'L97-128'.

FIG. 1 depicts stalks of 'L97-128', its female parent 'LCP81-10', and male parent 'LCP85-384'. A white wax bloom covers the stalk of 'L97-128', and is typically more abundant than the wax bloom of 'LCP85-384'. 'LCP81-10' exhibits less wax than 'LCP85-384'. The stalk color of each variety varies under a wax bloom (unexposed to sunlight). 'L97-128' exhibits a greenish-brown stalk [7.5 Y (yellow) 5/8] as compared to that of 'LCP85-384', which gradually changes from yellow [10 Y (yellow) 8.5/4] to green [between 2.5 G (green) Y(yellow) 5/6 and 2.5 G (green) Y (yellow) 6/6], and 'LCP81-10', which exhibits a predominantly green stalk [between 5 G (green) Y (yellow) 5/8 and 5 G (green) Y (yellow) 5/6]. (The stalk color of each variety becomes more red or purple when exposed to sunlight.) Colorimetric evaluations using the aforementioned color charts of the stalk, wax, and leaf for 'LCP81-10', 'LCP85-384', and 'L97-128' at harvest, are shown in Table 1.

'L97-128' emerges quickly after planting and exhibits an average, mature stalk height (ground level to the top visible dewlap) of 270 cm, as compared to that of 'LCP85-384' (222 cm), and 'LCP81-10' (217 cm). The average stalk diameter of 'L97-128' is 26 mm, as compared to that of 'LCP85-384' (22 mm dia) and 'LCP81-10' (27 mm dia). Each variety exhibits a cylindrically-shaped internode (fourth internode from ground level) and a glabrous (lacking hair) growth ring having a width of 0.3 mm. The root band of each variety is 0.7 mm wide, glabrous with straight sides, and exhibits unequally distributed rows of irregularly-shaped root primordia having a diameter of between about 0.25 and about 0.50 mm. The root band of 'L97-128' exhibits an extensive wax layer, as compared to that of 'LCP85-384' (light wax layer), and 'LCP81-10' (moderate wax layer). The internodes of 'L97-128' are smooth and glabrous with few, if any, corky patches or cracks, and exhibit an average length at the mid-culm of 18.2 cm. The internodes of 'L97-128' and 'LCP81-10' exhibit a moderate bud furrow, as compared to that of 'LCP 85-384', which exhibit no bud furrow. The buds of each variety are located just above the leaf scar, and are raised above the surface of the root band. 'L97-128' and 'LCP81-10' similarly exhibit a round bud shape (at the fourth node) with a central germ pore, as compared to that of 'LCP85-384', which is pentagonal. The bud diameter of both 'L97-128' and 'LCP81-10' is 7–9 mm, which is larger than that of 'LCP85-384'. The buds of 'L97-128' are 6–7 mm long and yellow [7.5Y (yellow) 7/8], without any wax surfaces. All three varieties exhibit no setaceous or pilose hairs on the buds. See Table 1.

Figure 2:
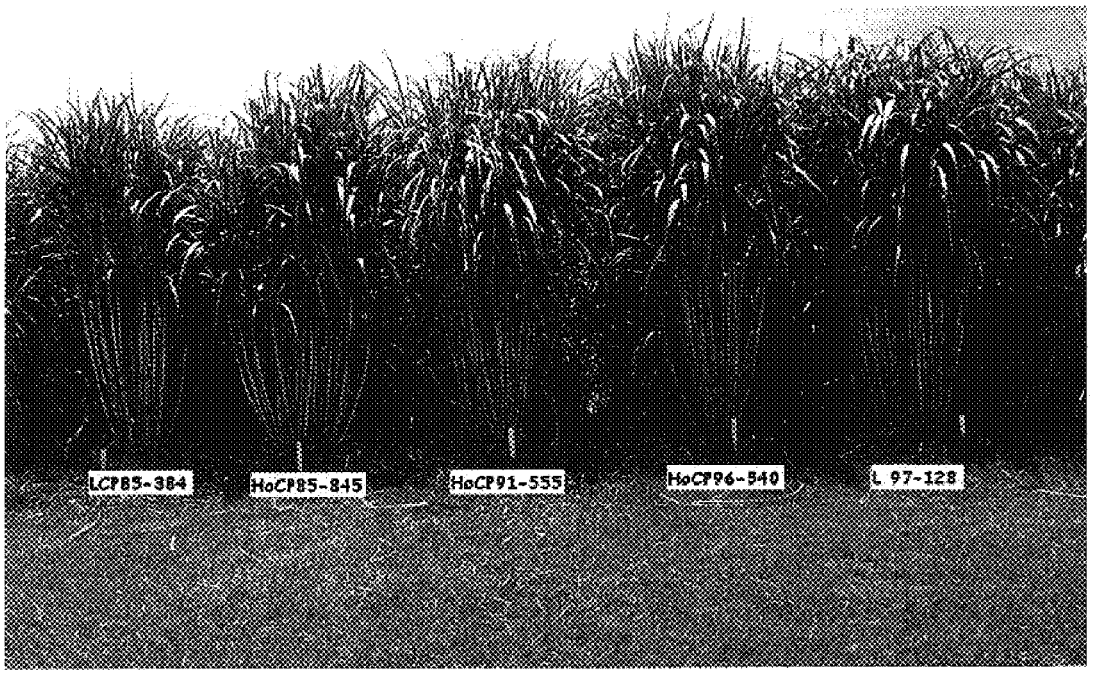
FIG. 2 is a color photograph of the canopy biomass of the novel variety of sugarcane identified as 'L97-128' and other sugarcane varieties identified as 'LCP85-384', 'HoCP85-845', 'HoCP91-555', and 'HoCP96-540', which were used for comparison tests.

FIG. 2 depicts the canopy biomass of the novel variety of sugarcane identified as 'L97-128' and other sugarcane varieties identified as 'LCP85-384', 'HoCP85-845' (unpatented), 'HoCP91-555' (unpatented), and 'HoCP96-540' (unpatented), which were used for comparison tests. The canopy of 'L97-128' and 'LCP81-10' (not shown) droops, while that of 'LCP85-384' is more erect. See B. L. Legendre, et al., "Registration of 'HoCP85-845' Sugarcane," *Crop Sci.,* vol. 34, p. 820 (1994); B. L. Legendre, et al., "Registration of 'HoCP91-555' Sugarcane," *Crop Sci.,* vol. 40, p. 1506 (2000); and T. L. Tew, et al., "Registration of 'HoCP96-540' Sugarcane," *Crop Sci.,* vol. 44 (2004; in press).

Figure 3:
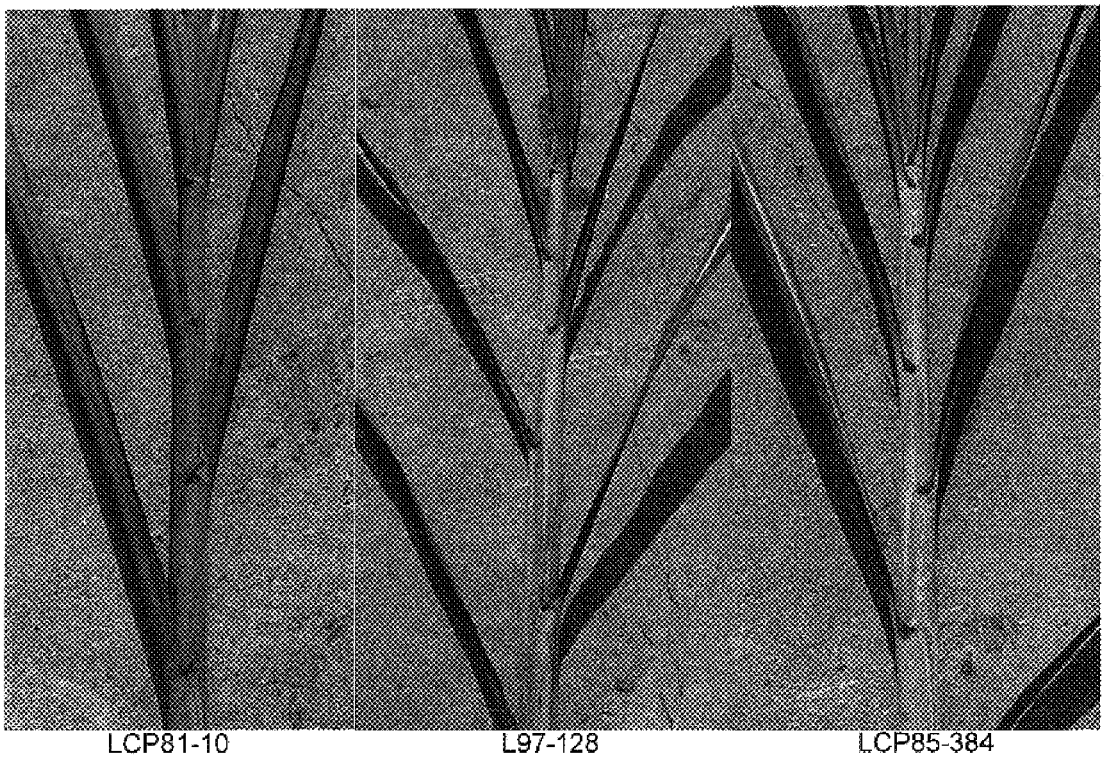
FIG. 3 is a color photograph of the leaf sheath, dewlaps (leaf collars), and auricles of the novel variety of sugarcane identified as 'L97-128' and other sugarcane varieties identified as 'LCP85-384' and 'LCP81-10', which were used for comparison tests.

FIG. 3 depicts the upper leaf sheaths, dewlaps (leaf collars), and auricles of 'LCP81-10', 'L97-128', and 'LCP85-384'. The average leaf blade length and width of 'L 97-128', 'LCP 81-10', and 'LCP 85-384', at the third leaf below the top most visible dewlap, are 160 cm and 34.1 mm, 158 cm and 44.5 mm, and 137 cm and 35.9 mm, respectively. 'LCP81-10' and 'L97-128' similarly exhibit green leaf blades which gradually change from [7.5 G(green) Y(yellow) 5/4] to [7.5 G(green) Y(yellow) 4/4] at the second visible dewlap, as compared to that of 'LCP85-384' which exhibits a lighter green color changing from [7.5 G(green) Y(yellow) 5/6] to [7.5 G(green) Y(yellow) 4/6] at the second visible dewlap. Each of these varieties exhibit acuminate leaf blades. 'L97-128' and 'LCP81-10' similarly exhibit a 4–8 mm wide mid-rib distinctly raised on its abaxial side, as compared to that of 'LCP85-384' which is 3–7 cm wide. The mid-rib of 'L97-128' is the same color as the leaf blade on the abaxial side. On the adaxial side, the mid-rib of 'L97-128' has a smooth to concave surface and a whitish color [5Y(yellow) 9/2] lighter than its leaf blade. Both the leaf blade and mid-rib of 'L97-128' are linear, glabrous with a smooth surface, and relatively thin. The dewlaps of 'LCP81-10', 'L97-128', and 'LCP85-384' are narrow and square-shaped with a brownish color [5Y(yellow) 4/4]. 'LCP85-

384' exhibits a distinct, necrotic leaf sheath margin, which is more prominent than 'L97-128' and 'LCP81-10'. The average auricle shape for both 'L97-128' and 'LCP81-10' is short lanceolate, as compared to that of 'LCP 85-384', which is slightly shorter. (Auricles were measured on the fourth leaf from the top most visible dewlap.) 'L97-128' and 'LCP81-10' exhibits a linear crescent-shaped ligule, while that of 'LCP85-384' is broad crescent. 'L97-128' exhibits a tan color ligule color [2.5 Y (yellow) 6/2] having a length of 1.5–2.0 mm and a width of 13–15 mm, with a torn, darker brown [5 Y (yellow) 2/2] edge. The ligule region of 'L97-128' exhibits no pubescence. See Table 1.

TABLE 1

| Trait | 'L97-128' | 'LCP85-384' | 'LCP81-10' |
|---|---|---|---|
| Stalk Height (cm) (Avg. 10 stalks) | 270 | 222 | 217 |
| Stalk Cum Dia. (mm) (Avg. of 10 stalks) | 26 | 22 | 27 |
| Leaf Shape | Drooping | Erect | Drooping |
| Leaf Length (cm) (Avg. of 10 leaves) | 160 | 137 | 158 |
| Leaf Width (mm) Avg. 10 leaves | 34.1 | 35.9 | 44.5 |
| Leaf Color | 7.5 GY 5/4 to 7.5 GY 4/4 | 7.5 GY 5/6 to 7/5 GY 4/6 | 7.5 GY 5/4 to 7.5 GY 4/4 |
| Wax | BG-PB 7/10B | BG-PB 7/10B | BG-PB 7/10B |
| Stalk Color | 7.5 Y 5/8 | 10 Y 8.5/4 to 2.5 GY 5/6 & 6/6 | 5 GY 5/8 to 5 GY 5/6 |
| Stalk Buds Shape (4th node) | Round bud with central germ pore | Pentagonal bud | Round bud with central germ pore |
| Auricle | Short Lanceolate | Short Lanceolate | Short Lanceolate |
| Shape | | | |
| Length (mm) Avg. of 5 auricles | 7 | 6 | 7 |
| Internode | Extensive | Light | Moderate |
| Waxiness | Moderate | None | Moderate |
| Bud Furrow | 0.3 mm | 0.3 mm | 0.3 mm |
| Growth Ring Width | 0.7 mm | 0.7 mm | 0.7 mm |
| Root Band Width | Cylindrical | Cylindrical | Cylindrical |
| Stalk Shape (4th internode from ground level) | | | |
| Ligule Shape | Linear Crescent | Broad Crescent | Linear Crescent |
| Leaf Sheath | Moderate Pubescence (on green leaves) | Extensive Pubescence (on green leaves) | Light Pubescence (on green leaves) |
| Flesh Color | 7/4 10Y | 8.5/4 10Y | 8/4 5Y |
| Growth Ring Surface | Glabrous | Glabrous | Glabrous |
| Leaf Scar Shape | Oblique | Horizontal | Horizontal |
| Leaf Sheath Length (cm) | 33.8 | 34.2 | 37.3 |
| Leaf Sheath Color | 5/4 5GY | 5/6 5GY | 5/6 2.5GY |

Figure 4:
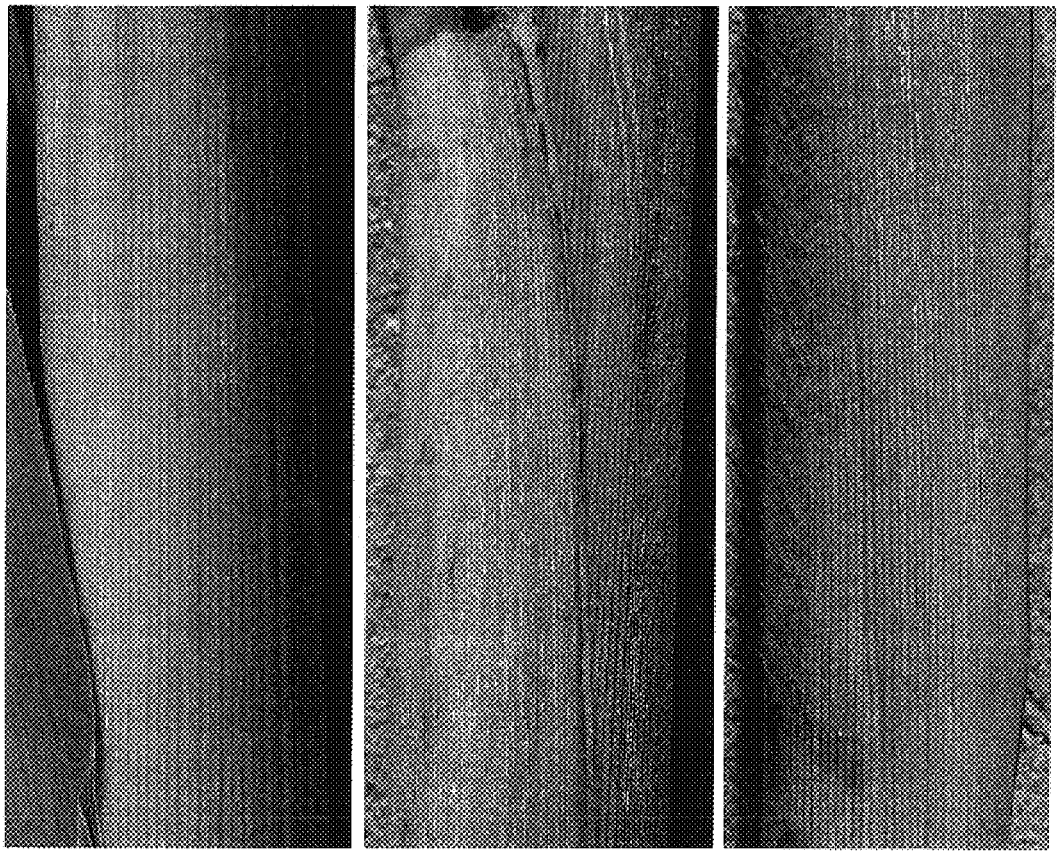
FIG. 4 is a color photograph of the pubescence on the leaf sheath of the novel variety of sugarcane identified as 'L97-128' and other sugarcane varieties identified as 'LCP85-384' and 'LCP81-10', which were used for comparison tests.

FIG. 4 depicts the pubescence on the leaf sheaths of 'LCP81-10', 'L97-128', and 'LCP 85-384'. On the abaxial side of the leaf sheath, 'L97-128' exhibits a moderate amount of setaceous hair, when compared to 'LCP85-384', which is extensive. The leaf sheath pubescence of 'L97-128' is predominately opposite of the dewlap of the next lower leaf. 'LCP81-10' exhibits a more glabrous leaf sheath than 'L97-128'.

Under normal growing conditions in Louisiana, 'L97-128' does not exhibit any flowering. The following flower description was obtained from a 38 L can culture of 'L97-128' grown in St. Gabriel, La., on Oct. 4, 2004 (approximately 130–145 days in age from spring emergence). 'L97-128' exhibited a cylindrical-shaped inflorescence peduncle, degenerating from the base, having a width and length of approximately 6 mm and 40–50 mm, respectively, and pubescence throughout, with short, appressed, silvery pilose hairs [R (red)-Y (yellow) 9/10Y (yellow)]. 'L97-128' has a 600–610 mm long inflorescence main axis with some pilose hairs. Primary branches of 'L97-128' are 295–320 mm long and exhibit appressed racemose branches. Rachis internodes of 'L97-128' are glabrous from the bottom of the main axis, and exhibit a few setaceous hairs towards the apex of the main axis. The apex of 'L97-128' is predominantly grooved. Sessile spikelets of 'L97-128' are 2.5–3.0 mm long with callus hairs having a length of 9–13 mm and a white color [R (red)-Y (yellow) 9/10Y (yellow)]. The sessile spikelets of 'L97-128' are lanceolate, acuminate, and have membranous glumes, lemma with a hyaline scale, and yellow stamens [(Y yellow)-G (green) 3.75Y (yellow)] 1.5–2.0 mm long. Pedicellate spikelets of 'L97-128' are ovate, acute, rounded at the base, and 2.5–3.0 mm long. The glumes of the pedicillate spikelets of 'L97-128' are membranous; the lemma is hyaline; and the stamens are yellow [Y (yellow)-G (green) 3.75Y (yellow)].

Example 1

Test Conducted

To confirm that 'L97-128' was a new variety, controlled tests (e.g., pathogen responses and yield), were conducted in St. Gabriel, La. Fifty-one mechanically harvested, outfield variety trials conducted across south Louisiana involving the replication of 'LCP85-384', 'HoCP85-845', 'HoCP91-555', and 'HoCP96-540' were selected for comparison tests with 'L 97-128' because of their commercial dominance in the Louisiana sugarcane market. Diseases that commonly affect the growth of sugarcane were selected to test for pathogen responses in all the varieties. 'LCP81-10', 'LCP85-384', and 'L97-128' exhibited similar resistance to sugarcane mosaic and sorghum mosaic viruses. 'L97-128' exhibited moderate susceptibility to smut (caused by *Ustilago scitaminea* Sydow & P. Sydow), unlike 'LCP81-10' and 'LCP85-384', which both exhibited resistance to smut. 'L97-128' and 'LCP81-10' similarly exhibited moderate resistance to rust (caused by *Puccinia melanocephala* H. and P. Sydow), unlike 'LCP85-384', which exhibited susceptibility to this disease. 'LCP81-10', 'LCP85-384', and 'L97-128' similarly exhibited resistance to leaf scald (caused by *Xanthomonas albilineans* Ashby, Dowson), under natural field infection conditions. The effect of yellow leaf syndrome on the yield of 'L97-128' and its parents are unknown. Similar to both of its parents and all other sugarcane varieties grown in Louisiana, 'L97-128' exhibited significant yield loss in ratoon crops from ratoon stunning disease (caused by *Clavibacter xyli* subsp. *xyli* Davis). 'L97-128' and 'LCP85-384' are both susceptible to the sugarcane borer (caused by *Diatraea saccharalis* Fabricius) insect pest of sugarcane. The reaction of 'LCP 81-10' to sugarcane borer is unknown. Field observations show that 'L97-128' is no more susceptible to herbicides commonly used for weed control than 'LCP85-384'. Sugarcane disease and sugarcane borer ratings of 'L97-128', 'LCP81-10', and 'LCP85-384' are shown in Table 2.

No other formal trials have been conducted to date on 'L97-128' for other insect pests. 'L97-128' does not appear to show any novel insect resistance.

TABLE 2

| Variety | Mosaic | Smut | Rust | Leaf Scald | Ratoon Stunting Disease | Sugar-cane Borer |
|---|---|---|---|---|---|---|
| 'L97-128' | R | MS | MR | R | S | S |
| 'LCP81-10' | R | R | MR | R | S | U |
| 'LCP85-384' | R | R | S | R | S | S |

"R" — Resistant; "MR" — Moderately Resistant; "S" — Susceptible; "MS" — Moderately Susceptible; and "U" — Unknown To determine yield, fifty-one mechanically harvested, outfield variety trials involving the replication of 'L97-128', 'LCP85-384', 'HoCP85-845', 'HoCP91-555', and 'HoCP96-540' ('HoCP 96-540' is a half-sibling of 'L97-128', sharing the same male parent 'LCP85-384') were conducted between the years 2001 and 2003 and various locations within Louisiana. The varieties were planted in Balwin silty clay loam in St. Mary Parish, Commerce silt loam in Pointe Coupee Parish, Commerce silt loam in St. James Parish, Commerce silt loam in Lafourche Parish, Commerce silt loam in Assumption Parish, Jeanerette silt loam in Iberia Parish, Patout silt loam in St. Martin Parish, Commerce silt loam in St. John the Baptist Parish, and Sharkey clay in Terrebonne Parish. Each block/plot was fertilized with nitrogen, potassium, and phosphorous according to standard farm practices associated with each operation. 'L97-128' produced an average fiber content of 12.2% after twenty trials, which was slightly higher than the 11.1% average fiber content produced by 'LCP85-384'. Data for sugar yield, cane yield, sucrose content, stalk weight, and stalk number are shown in Table 3.

TABLE 3

| Variety | Sugar Yield (Mt/ha) | Cane Yield (Mt/ha) | Sucrose Content [%)/Mt] | Stalk Weight (kg) | Stalk Number (stalks/ha) |
|---|---|---|---|---|---|
| | | Plant-cane crop (28)† | | | |
| 'LCP85-384' | 8.64 | 65.9 | 13.1 | 0.98 | 68525 |
| 'HoCP85-845' | 8.11− | 65.6 | 12.4− | 1.08+ | 61179− |
| 'HoCP91-555' | 8.56 | 65.0 | 13.2 | 0.98 | 67466 |
| 'HoCP96-540' | 9.78+ | 73.7+ | 13.3 | 1.22+ | 61622− |
| 'L97-128' | 9.68+ | 72.4+ | 13.4 | 1.21+ | 60293− |
| | | First ratoon crop (16)† | | | |
| 'LCP85-384' | 8.82 | 62.7 | 13.6 | 0.82 | 78477 |
| 'HoCP85-845' | 7.95− | 61.2 | 13.1− | 0.93+ | 67471− |
| 'HoCP91-555' | 7.97 | 57.8− | 13.8 | 0.82 | 71168− |
| 'HoCP96-540' | 8.69 | 64.7 | 13.5 | 1.00+ | 65645− |
| 'L97-128' | 8.65 | 62.3 | 14.0+ | 1.00+ | 62187− |
| | | Second ratoon crop (7)† | | | |
| 'LCP85-384' | 7.05 | 53.8 | 13.2 | 0.72 | 74634 |
| 'HoCP85-845' | 6.53 | 53.8 | 12.2− | 0.86+ | 63029− |
| 'HoCP91-555' | 7.30 | 53.3 | 13.8+ | 0.74 | 72939 |
| 'HoCP96-540' | 7.10 | 54.9 | 13.0 | 0.84+ | 65010− |
| 'L97-128' | 7.58 | 54.7 | 14.0+ | 0.87+ | 64390− |

†Number in parentheses represents the total number of trials. Varieties that are significantly higher or lower than 'LCP85-384' are denoted by a plus (+) or minus (−), respectively. The analysis was performed using the SAS (v 9.0) statistical software package (SAS Institute Inc., Cary, North Carolina).

Plant-cane maturity tests were conducted in Chacahoula, La. to compare the percentage of sucrose content per ton of cane of 'L97-128', 'LCP 85-384', 'HoCP85-845', 'HoCP91-555', and 'HoCP96-540'. 'L 97-128' demonstrated early maturity and continued to accumulate sucrose throughout the harvest, as shown in Table 4. 'L97-128' exhibited an 11.1% higher recoverable sucrose content in the plant-cane crop than 'LCP85-384', when harvested in mid-September 2003, as shown in Table 4. 'L97-128' exhibited a 32.4% higher recoverable sucrose content than 'LCP 85-384' when the first ratoon was harvested in August 2003 as shown in Table 5.

TABLE 4

| Variety | 2003 HARVEST DATES 9/23 | 10/21 | 11/18 | Average by Variety |
|---|---|---|---|---|
| 'LCP85-384' | 9.0 | 12.3 | 14.4 | 11.9 |
| 'HoCP85-845' | 9.0 | 12.3 | 13.7− | 11.7 |
| 'HoCP91-555' | 9.8 | 12.7 | 14.8 | 12.4+ |
| 'HoCP96-540' | 9.0 | 12.5 | 13.8− | 11.8 |
| 'L97-128' | 10.0+ | 12.8 | 14.8 | 12.5+ |
| Average by Date | 9.4 | 12.5 | 14.3 | 12.1 |

†Varieties that are significantly higher or lower than 'LCP85-384' are denoted by a plus (+) or minus (−), respectively, next to the value for each trait.

TABLE 5

| Variety | 2003 HARVEST DATES 8/25 | 9/08 | 9/23 | 10/06 | 10/21 |
|---|---|---|---|---|---|
| LCP85-384 | 7.4 | 9.3 | 10.4 | 11.7 | 12.8 |
| HoCP85-845 | 8.4 | 10.2 | 11.1 | 11.6 | 13.6+ |
| HoCP91-555 | 8.6+ | 9.9 | 11.1 | 12.3 | 14.0+ |
| HoCP96-540 | 8.0 | 9.0 | 10.3 | 11.3 | 12.8 |
| L97-128 | 9.8+ | 11.3+ | 12.1+ | 13.3+ | 14.9+ |
| Ave. by Date | 8.5 | 9.9 | 11.0 | 12.0 | 13.6 |

| Variety | 2003 HARVEST DATES 11/03 | 11/18 | 12/01 | Ave. by Variety |
|---|---|---|---|---|
| LCP85-384 | 13.4 | 15.1 | 15.4 | 11.9 |
| HoCP85-845 | 14.0 | 15.0 | 15.1 | 12.4+ |
| HoCP91-555 | 14.4+ | 15.7+ | 15.5 | 12.7+ |
| HoCP96-540 | 13.6 | 15.2 | 15.2 | 11.9 |
| L97-128 | 15.3+ | 16.4+ | 16.0+ | 13.6+ |
| Ave. by Date | 14.2 | 15.5 | 15.4 | 12.8 |

†Varieties that are significantly higher or lower than LCP85-384 are denoted by a plus (+) or minus (−), respectively, next to the value for each trait.

We claim:

1. A new and distinct variety of *Saccharum* sp. plant named 'L97-128', as described and illustrated in the specification herein.

* * * * *

LCP81-10 L97-128 LCP85-384